United States Patent
Tanhehco et al.

(10) Patent No.: US 7,828,831 B1
(45) Date of Patent: Nov. 9, 2010

(54) HOT AND COLD FLUID THERAPY SYSTEM

(75) Inventors: Benny L. Tanhehco, Powell, TN (US); Eric A. Ward, Knoxville, TN (US); Warren S. Bennett, Strawberry Plains, TN (US); Autry O. V. Debusk, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 1538 days.

(21) Appl. No.: 11/005,807

(22) Filed: Dec. 6, 2004

(51) Int. Cl.
*A61F 7/00* (2006.01)

(52) U.S. Cl. .......................... 607/104; 607/96; 607/108

(58) Field of Classification Search .................. 607/96, 607/104–112
See application file for complete search history.

(56) References Cited

U.S. PATENT DOCUMENTS

| 2,726,658 A | 12/1955 | Chessey |
| 3,477,427 A | 11/1969 | Lapidus |
| 3,918,458 A | 11/1975 | Nethery |

(Continued)

FOREIGN PATENT DOCUMENTS

| EP | 0 672 401 A2 | 9/1995 |

(Continued)

OTHER PUBLICATIONS

T-300 Motorized Cold Therapy Unit Author: unknown date of publication: unknown The T-300 is a soft bag cold therapy device utilizing a pump to circulate cold water through an applicator. The T-300 used a thermistor as the fluid temperature sensor which was located in the outlet conduit of the bag. The unit also used a thermistor sensor at the fluid return line just prior to the fluid's entry into the fluid reservoir from the applicator to monitor the temperature of the returned fluid to control the fluid flow rate and thus the temperature of the fluid at the applicator. The first date of sale was Dec. 1, 1999.

*Primary Examiner*—Roy D Gibson
(74) *Attorney, Agent, or Firm*—Luedeka, Neely & Graham, PC (57) ABSTRACT

A temperature controlled fluid therapy system includes a reservoir for containing hot or cold fluid, a pump with a submersible motor disposed within the reservoir, a watertight blanket for containing the hot or cold fluid, and output and intake conduits for circulating the fluid between the reservoir and the blanket. The system includes a first temperature sensor disposed within the reservoir for measuring the temperature of the fluid in the reservoir, and a second temperature sensor disposed adjacent the blanket for measuring the temperature of the fluid in the blanket. A power supply provides power to the pump motor. A controller controls the power provided to the motor based upon the first and second temperature signals, thereby controlling the fluid flow rate through the blanket and hence the temperature of the fluid in the blanket. When the temperature of the fluid in the reservoir is within a hot temperature range, such as 90° F. to 120° F., the controller maintains the temperature of the fluid in the blanket within the hot temperature range. When the temperature of the fluid in the reservoir is within a cold temperature range, such as 45° F. to 65° F., the controller maintains the temperature of the fluid in the blanket within the cold temperature range.

17 Claims, 10 Drawing Sheets

U.S. PATENT DOCUMENTS

| | | | |
|---|---|---|---|
| 4,112,943 A | 9/1978 | Adams | |
| 4,459,468 A | 7/1984 | Bailey | |
| 4,640,284 A | 2/1987 | Ruderian | |
| 4,821,354 A | 4/1989 | Little | |
| 4,960,103 A | 10/1990 | Urso | |
| 5,097,829 A | 3/1992 | Quisenberry | |
| 5,174,285 A | 12/1992 | Fontenot | |
| 5,183,039 A | 2/1993 | Sarian et al. | |
| 5,241,958 A | 9/1993 | Noeldner | |
| 5,277,695 A | 1/1994 | Johnson, Jr. et al. | |
| 5,330,519 A | 7/1994 | Mason et al. | |
| 5,332,884 A * | 7/1994 | Bailey | 219/494 |
| 5,371,655 A | 12/1994 | Murdock et al. | |
| 5,476,489 A | 12/1995 | Koewler | |
| 5,528,485 A | 6/1996 | Devilbiss et al. | |
| 5,566,062 A | 10/1996 | Quisenberry et al. | |
| 5,647,051 A | 7/1997 | Neer | |
| 5,711,155 A * | 1/1998 | DeVilbiss et al. | 62/3.7 |
| 5,871,526 A * | 2/1999 | Gibbs et al. | 607/104 |
| 5,895,418 A | 4/1999 | Saringer | |
| 5,980,561 A * | 11/1999 | Kolen et al. | 607/104 |
| 6,551,348 B1 | 4/2003 | Blalock et al. | |
| 6,645,232 B2 * | 11/2003 | Carson | 607/104 |
| 6,660,027 B2 * | 12/2003 | Gruszecki et al. | 607/104 |
| 7,306,568 B2 * | 12/2007 | Diana | 601/15 |
| 2004/0210283 A1 * | 10/2004 | Rose et al. | 607/96 |

FOREIGN PATENT DOCUMENTS

| | | |
|---|---|---|
| WO | WO 98/57064 | 12/1998 |

* cited by examiner

HOT AND COLD FLUID THERAPY SYSTEM

FIELD

This invention relates to the field of therapeutic medical devices. More particularly, this invention relates to a temperature controlled fluid therapy system providing hot or cold fluid therapy to an individual.

BACKGROUND OF THE INVENTION

Hot and cold therapies have been used for many years to treat physiological maladies. Ice application, one of the more traditional cold therapy methods, has the advantage of minimal cost and the ready availability of ice. However, traditional ice application methods are not perfect, as indicated by many patient complaints about leaky ice bags and the inconvenience of refilling the ice bag as the ice melts. Furthermore, traditional ice application methods are not very precise in applying a uniform temperature throughout the injured area. Likewise, the application temperature is not easily regulated.

Various mechanical cold and hot therapy systems have been developed to surmount some of the problems associated with the more traditional therapeutic techniques. However, not all of these mechanical fluid therapy systems provide constant temperature regulation which may be deleterious to patient recovery. Additionally, current temperature sensors used in therapy systems have been susceptible to the presence of a liquid, resulting in operational fluctuations, unrelated to temperature. These fluctuations make it impossible to control the system temperature precisely.

There is a need for an improved fluid therapy system that provides constant temperature regulation in hot and cold therapy applications.

SUMMARY

The above and other needs are met by a temperature controlled fluid therapy system that includes a reservoir for containing hot or cold fluid, a pump with a submersible motor disposed within the reservoir, a watertight blanket having an internal space through which the fluid may be circulated, and intake and output conduits for circulating the fluid between the reservoir and the blanket. The system includes a first temperature sensor disposed within the reservoir for generating a first temperature signal related to the temperature of the fluid in the reservoir. The system also includes second temperature sensor disposed adjacent the blanket for generating a second temperature signal related to the temperature of the fluid in the blanket. A power supply provides power to the pump motor, and a controller controls the power provided to the motor based upon the first and second temperature signals. In this manner, the controller controls the rate of fluid flow through the blanket and hence the temperature of the fluid in the blanket.

When the temperature of the fluid in the reservoir is within a hot temperature range, such as about 90° F. to 120° F., the controller controls the power provided to the pump motor to maintain the temperature of the fluid in the blanket within the hot temperature range. When the temperature of the fluid in the reservoir is within a cold temperature range, such as about 32° F. to 65° F., the controller controls the power provided to the pump motor to maintain the temperature of the fluid in the blanket within the cold temperature range.

In a preferred embodiment, the therapy system includes a display device for displaying messages to a user of the system. When the first temperature signal indicates that the temperature of the fluid in the reservoir is below the hot temperature range by a predetermined amount, the controller causes the display device to display a message indicating that hot fluid should be added to the reservoir. When the first temperature signal indicates that the temperature of the fluid in the reservoir is above the cold temperature range by a predetermined amount, the controller causes the display device to display a message indicating that ice should be added to the reservoir.

In another aspect, the invention provides a method for applying temperature controlled fluid therapy using a fluid therapy blanket. The method includes the steps of (a) adding fluid to a reservoir, (b) sensing the temperature of the fluid in the reservoir, (c) determining whether the temperature of the fluid in the reservoir is above a minimum temperature for cold therapy, (d) determining whether the temperature of the fluid in the reservoir is below a maximum temperature for cold therapy, and (e) pumping the fluid from the reservoir through the fluid therapy blanket when it is determined that the temperature of the fluid in the reservoir is above the minimum temperature and below the maximum temperature for cold therapy.

In a preferred embodiment, the method also includes the steps of (f) determining whether the temperature of the fluid in the reservoir is above a minimum temperature for hot therapy, (g) determining whether the temperature of the fluid in the reservoir is below a maximum temperature for hot therapy, and (h) pumping the fluid from the reservoir through the fluid therapy blanket when it is determined that the temperature of the fluid in the reservoir is above the minimum temperature and below the maximum temperature for hot therapy.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
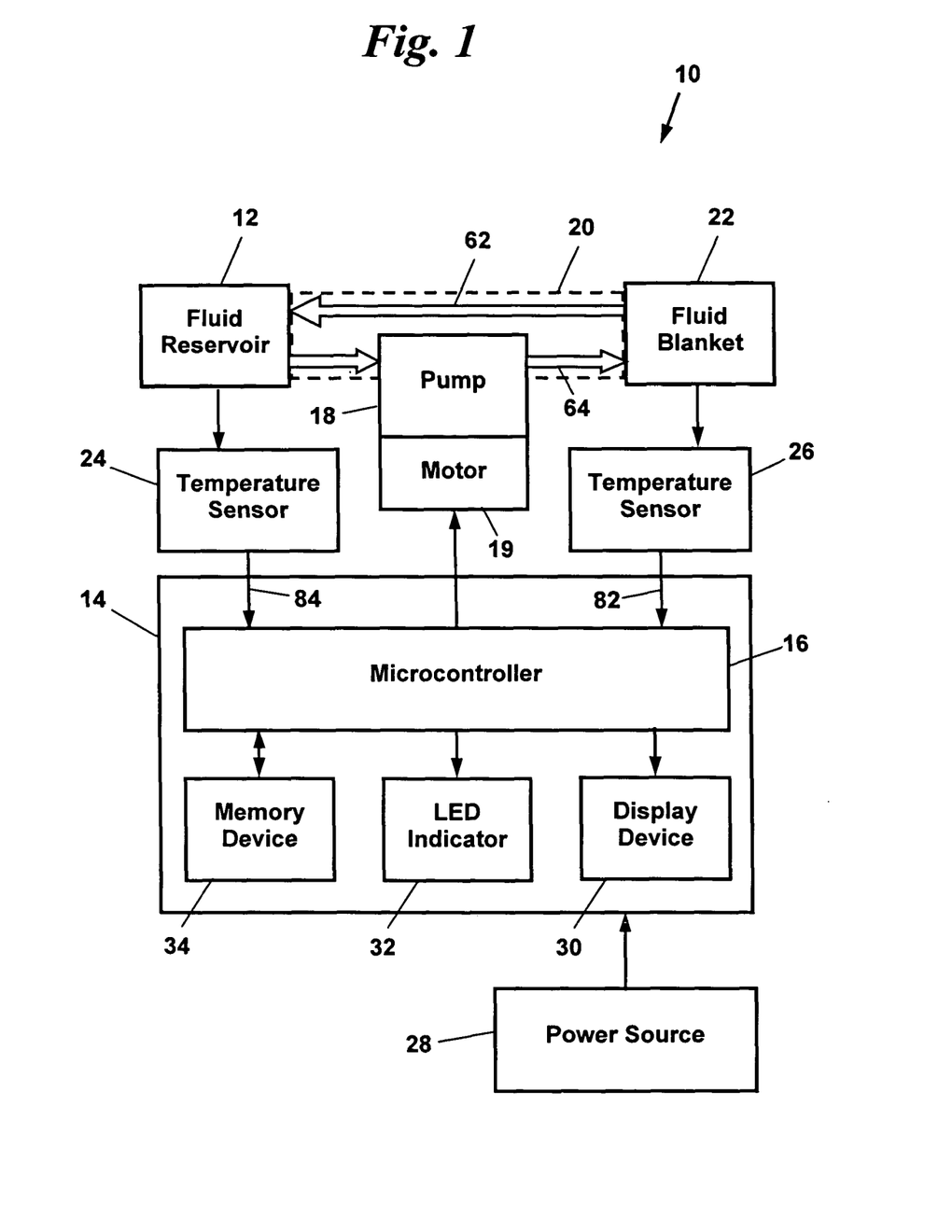
FIG. 1 is a functional block diagram of a fluid therapy apparatus according to a preferred embodiment of the invention.

FIG. 1 depicts a preferred embodiment of a temperature controlled fluid therapy device 10 for providing hot and cold fluid therapy to a user. The device 10 includes a fluid reservoir 12 (also referred to herein as a bucket) in fluid communication with a submersible pump 18 driven by a continuously variable motor 19, and a fluid blanket 22 in fluid communication with the pump 18 via a fluid conduit assembly 20. The device 10 also includes a microcontroller 16, memory 34, a multicolor LED indicator 32, two temperature sensors 24 and 26, a display device 30 and a power source 28. In the preferred embodiment of the invention, the microcontroller 16, memory 34, multicolor LED indicator 32 and display device 30 are attached to a single printed circuit board 14. Also in a most preferred embodiment, the memory 34 is internal to the microcontroller 16, which is also referred to herein as a microprocessor.

Figure 2A:
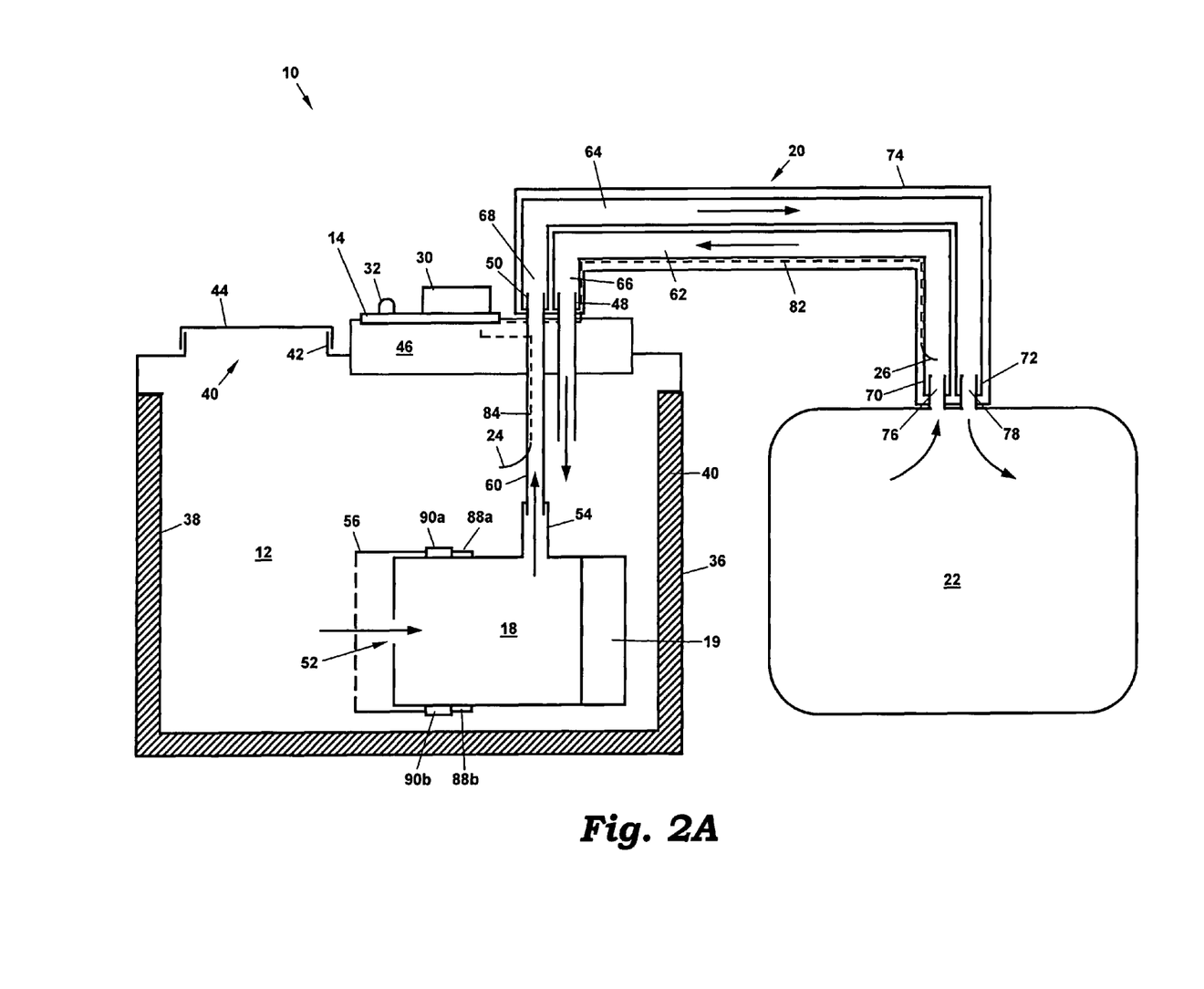
FIG. 2A depicts the configuration of a fluid therapy apparatus according to a preferred embodiment of the invention.

As shown in FIG. 2A, the fluid reservoir 12 preferably includes an outer jacket 36 and an interior liner 38 which form a cavity 40 there between. In a preferred embodiment, the outer jacket 36 and the liner 38 are constructed from thermoplastic using an injection molding or blow molding process. Preferably, the cavity 40 is filled with an insulating material such as urethane foam. Alternatively, the interior liner 38 may be constructed of an insulating material such as a structural foam, formed adjacent to the outer jacket 36. The fluid reservoir 12 includes a fill port 40 formed in the upper surface of the liner 38. The fill port 40 is generally circular in shape having a diameter of about 4 to 5 inches, and has a threaded neck 42 extending outward from the top surface of the inner liner 38 for receiving a threaded lid 44. The fluid reservoir 12 preferably has a fluid handling capacity of between about 4 and 6 liters.

In a preferred embodiment of the invention, the printed circuit board 14 is attached to an insert 46 that snaps into an aperture in the upper surface of the liner 38. Alternatively, the insert 46 may be attached to the liner 38 using an adhesive gasket or using mechanical fasteners, such as screws. The insert 46, which is preferably molded from plastic, includes an entry port 48 and an exit port 50 to which the conduit assembly 20 is coupled for receiving and expelling fluid into and out of fluid reservoir 12. Preferably, a cover is attached over the top of the insert 46 to protect the circuit board 14. Apertures are provided in the cover to allow a user to view the display 30 and the LED indicator 32.

The power source 28 preferably comprises a self contained 12 volt battery pack. In the preferred embodiment, the power source 28 also comprises a power connector attached to the printed circuit board 14 to which a DC power adapter may be connected to provide an external source of power.

As shown in FIG. 2A, the pump 18 is housed within the fluid reservoir 12. Preferably, the pump 18 has a throughput of between about ¼ and 10 gallons/hour. With reference to FIG. 1, the pump motor 19 receives continuously variable power from the power source 28 under control of the microcontroller 16. The pump 18 includes an intake port 52 and an output port 54. The output port 54 is coupled to an output conduit 60 which is coupled to the exit port 50 of the insert 46. When the pump 18 is operating, fluid within reservoir 12 is drawn into the intake port 52 and forced out through the output port 54.

In the preferred embodiment depicted in FIG. 2A, the pump 18 is suspended from the output conduit 60. The output conduit 60 of this embodiment is somewhat flexible which allows for some movement of the pump 18 during shipment and normal use.

Preferably, a strainer 56 is disposed over the intake port 52 of the pump 18 to prevent foreign matter in the fluid from entering the pump 18. A pair of tabs 88a-88b extend from opposite edges of the strainer 56 and engage slots 90a-90b on opposite sides of the pump 18, thereby securing the strainer 56 to the pump 18.

Figure 2B:
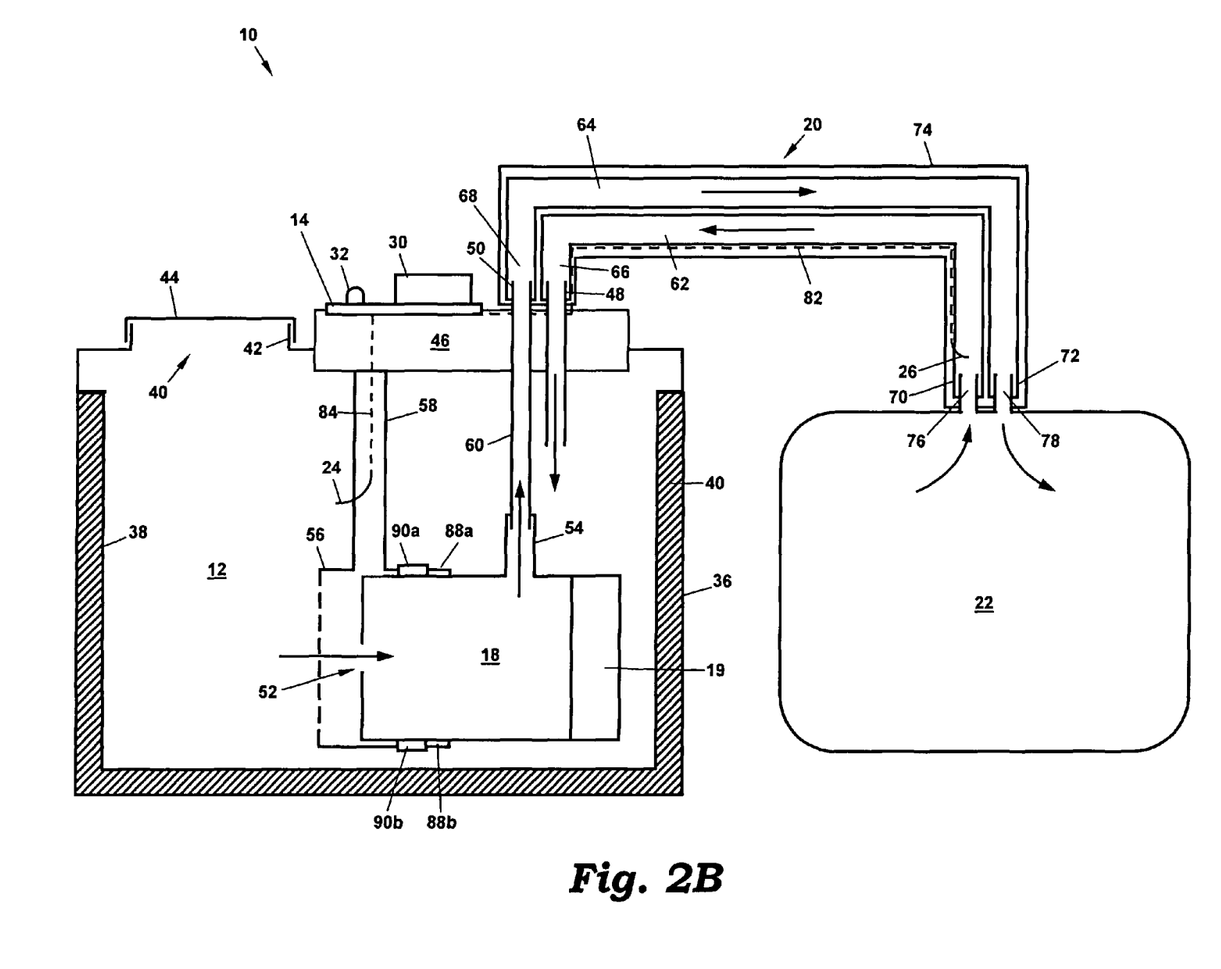
FIG. 2B depicts the configuration of a fluid therapy apparatus according to an alternative embodiment of the invention.

As shown in FIG. 2B, in one embodiment of the invention the strainer 56 includes a strainer bracket 58 extending outward there from. In this embodiment, the strainer 56 and strainer bracket 58 are integral plastic structures, such as polycarbonate, formed during a single molding process. A distal end of the strainer bracket 58 is attached to the insert 46, such as by a snap fit attachment or by screws.

In an alternative embodiment of the invention, a hand pump may also be included to provide an alternative pump means for the device 10. The hand pump is preferably disposed adjacent the fluid conduit 20, and includes two one-way check valves for pumping fluid through the fluid circuit. If a motorized pump is not included in device 10, or if the motorized pump is inoperable or malfunctioning, the hand pump is effective to pump fluid between the reservoir 12 and the fluid blanket 22.

As shown in FIGS. 1 and 2, the fluid conduit assembly 20 preferably comprises two elongate tubes, referred to herein as an intake conduit 62 and an output conduit 64, each having first ends 66 and 68, and second ends 70 and 72, respectively. In the preferred embodiment, the intake conduit 62 and the output conduit 64 are enclosed within a flexible insulating jacket 74 of material such as foam rubber or foam plastic. Since there is little heat transfer into or out of the insulating jacket 74, it tends to keep the fluid circulating within the intake and output conduits 62 and 64 at a relatively constant temperature. Preferably the intake conduit 62 and output conduit 64 have diameters of between about 0.25 and 0.75 inch and lengths of between about 4 and 8 feet. The second ends 70 and 72 of the intake and output conduits are coupled to an outflow connector 76 and an inflow connector 78, respectively, on the fluid blanket 22. Thus, as shown in FIG. 2A, a complete fluid circuit is formed between the fluid reservoir 12 and the fluid blanket 22 through the intake and output conduits 62, 64.

Figure 3:
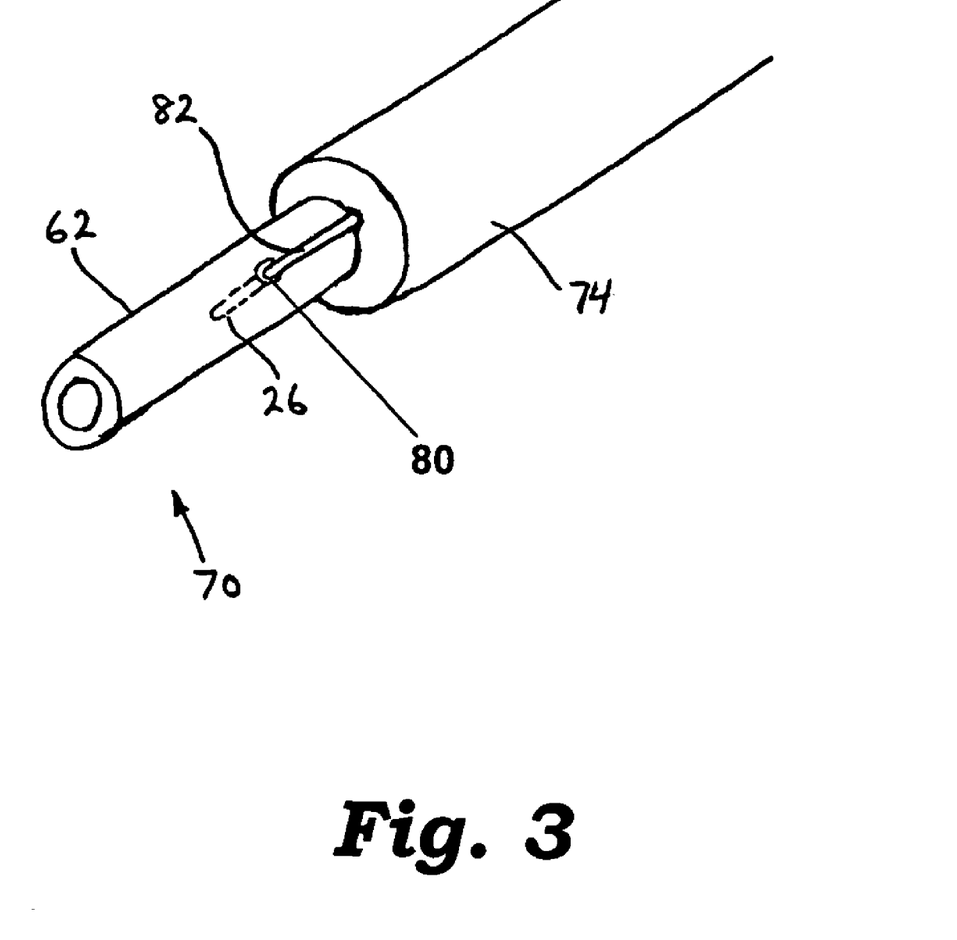
FIG. 3 depicts a thermocouple mounting location in a fluid therapy apparatus according to a preferred embodiment of the invention.

During application of hot/cold fluid therapy, it is preferable to maintain the fluid in a desired temperature range to provide maximum benefit to the user. To obtain an accurate reading of the temperature of the fluid within the fluid blanket 22, it is preferable to sense the temperature of the fluid as close as possible to the blanket 22. As shown in FIG. 3, the fluid temperature is preferably sensed inside the input conduit 62 at a location adjacent its second end 70. This location tends to give a close approximation of the temperature of the fluid circulating through the blanket 22. In the preferred embodiment, the hot junction of the thermocouple 26 is inserted through a small hole the conduit 62 so that it extends into the fluid path. The hole is preferably sealed using an epoxy bead 80. The thermocouple wire 82 to the printed circuit board 14 is preferably routed between the outer surface of the conduit 62 and the inner surface of the insulating jacket 74.

With reference to FIG. 2A, the hot junction of the thermocouple 24 within the reservoir 12 extends outward from the conduit 60. During normal use of the device 10, this attachment location places the sensor 24 below the surface of the fluid in the fluid reservoir 12, which is an ideal location for measuring the temperature of the fluid there. The thermocouple wire 84 that connects the hot junction of the thermocouple 24 to the printed circuit board 14 is preferably attached to the conduit 60 by means of an adhesive.

In the alternative embodiment depicted in FIG. 2B, the hot junction of the thermocouple 24 within the reservoir 12 extends outward from the strainer bracket 58. In this embodiment, the thermocouple wire that connects the hot junction of the thermocouple 24 to the printed circuit board 14 is preferably routed through the strainer bracket 58.

The preferred embodiment of the invention incorporates temperature sensors that tend to be impervious to fluid permeation, such as thermocouple sensors. Accordingly, the sensors 24 and 26 are preferably T-type thermocouples having a constantan member and a copper member. However, K-type thermocouples consisting of a chromell member and alumel member, or other types of temperature sensors, could also be used. The thermocouple sensors 24 and 26 preferably include a cold junction and a hot junction, and the output signals from the sensors 24 and 26 are proportional to the temperature difference between their respective cold and hot junctions. Since the output signal of a thermocouple sensor is generally proportional to the temperature difference between the cold and hot junctions, the thermocouple sensor does not provide an absolute temperature indication. Preferably, a thermistor mounted on the circuit board 14 and a 5 V reference voltage provide cold junction compensation, thereby making it possible to determine the absolute temperature at the hot junctions of the thermocouple sensors 24 and 26.

Exemplary values of temperature versus amplified thermocouple output voltage is shown in Table I. A linear approximation for the voltage-to-temperature relationship may be expressed as:

$$VT = \frac{\Delta \text{voltage}}{\Delta \text{temperature}} = \frac{3.48 - 3.09 \text{ V}}{64 - 38°\text{F.}} = 15 \text{ mV/°F.}$$

TABLE I

| Temperature (° F.) | Thermocouple Voltage (V) |
| --- | --- |
| 120 | 4.32 |
| 90 | 3.87 |
| 64 | 3.48 |
| 50 | 3.27 |
| 46 | 3.20 |
| 38 | 3.09 |

The microcontroller 16 of the preferred embodiment is a Microchip PIC16C72A having a built-in 10-bit analog-to-digital converter (ADC) for digitizing the output voltages of the thermocouple sensors 24 and 26. The 5 volts which provides a reference for the thermocouple signals also preferably provides the reference voltage for the ADC. Accordingly, the ADC has an input voltage range of 0-5V which results in the following quantization relationship:

$$Q = \frac{\text{fullscale voltage}}{2^{N \text{ bits}}} = \frac{5 \text{ volt}}{1024 \text{ bits}} = 4.88 \text{ mV/bit.}$$

Thus, the resolution of the system in terms of temperature is given as:

$$R = \frac{VT}{Q} = \frac{15 \text{ mV/°F.}}{4.88 \text{ mV/bit}} = 3.07 \text{ bits/°F.}$$

Table II shows the ADC conversion values for the data endpoints from Table 1, which can be used to determine a linear equation to convert from an ADC value to a temperature value.

TABLE II

| Temperature (° F.) | Voltage (V) | ADC value (10-bits) |
| --- | --- | --- |
| 120 | 4.32 | 885 |
| 38 | 3.09 | 633 |

Preferably, the ADC conversion values are stored in the memory 34. According to the preferred embodiment of the invention, the equation to convert from an ADC value to temperature is:

$$T = (ADV \text{ value} - Z_{intercept}) \times \frac{\text{Run}}{\text{Rise}} \quad (1)$$

(1)

where
Run=change in temperature.
Rise=change in ADC value, and
$Z_{intercept}$ is the ADC value at T=0.

In the preferred embodiment, to maintain the blanket temperature at about 45° F. for cold therapy use or above about 90° F. for hot therapy use, the microcontroller 16 adjusts the speed of the pump motor 19 to cause the fluid from the reservoir 12 to flow through the blanket 22 at the desired rate. To control the speed of the pump motor 19, the microcontroller 16 modulates the width of a pulse which is used to control the operation of the pump motor 19. More specifically, the duty cycle of the pulse width modulated signal is continuously varied according to the varying temperature of the fluid in the blanket 22 and the reservoir 12 as sensed by the thermocouple sensors 26 and 24. The varying pulse duty cycle output from the microcontroller 16 controls the average power delivered to the pump motor 19 from power source 28, thereby controlling the speed of the pump 18.

Depending on whether fluid therapy device 10 is being used in a cold therapy mode or a hot therapy mode, the microcontroller 16 controls the speed of the pump motor 19 accordingly. Generally, in a cold fluid therapy application, as the temperature of the fluid in the blanket 22 increases above a predetermined threshold (and other criteria are met), the microcontroller 16 causes the duty cycle of the power pulses from the power source 28 to increase, thereby causing the pump rate to increase which increases the flow of cool fluid flowing from within reservoir 12 to the blanket 22. If the temperature in the blanket 22 decreases below a predetermined threshold (and other criteria are met), the duty cycle of the power pulses will correspondingly decrease to a point where the pump 18 is nearly stopped. For a hot fluid therapy application, as the temperature of the fluid in the blanket 22 decreases below a predetermined threshold, the microcontroller 16 will cause the duty cycle of the power pulses from the power source 28 to increase, causing the rate of the pump 18 to increase, thereby increasing the flow of hot fluid from the reservoir 12 to the blanket 22. The conditions which cause the microcontroller 16 to increase or decrease the duty cycle of power supplied to the pump motor 19 are described in more detail hereafter.

Firmware Operation

Preferred methods for operating the system 10 in hot and cold therapy modes is depicted in the flowcharts of FIGS. 4-9. These flowcharts also describe preferred methods for calibrating and initializing the system 10. One skilled in the art will appreciate that variations may be made to these flowcharts while still accomplishing preferred methods for operating the system. Thus, it should be understood that the invention is not limited to any particular flowchart sequence or programming logic. Accordingly, it should be appreciated that the flowcharts of FIGS. 4-9 and the accompanying description of those flowcharts are provided merely as one example of the operation of the invention.

Figure 8:
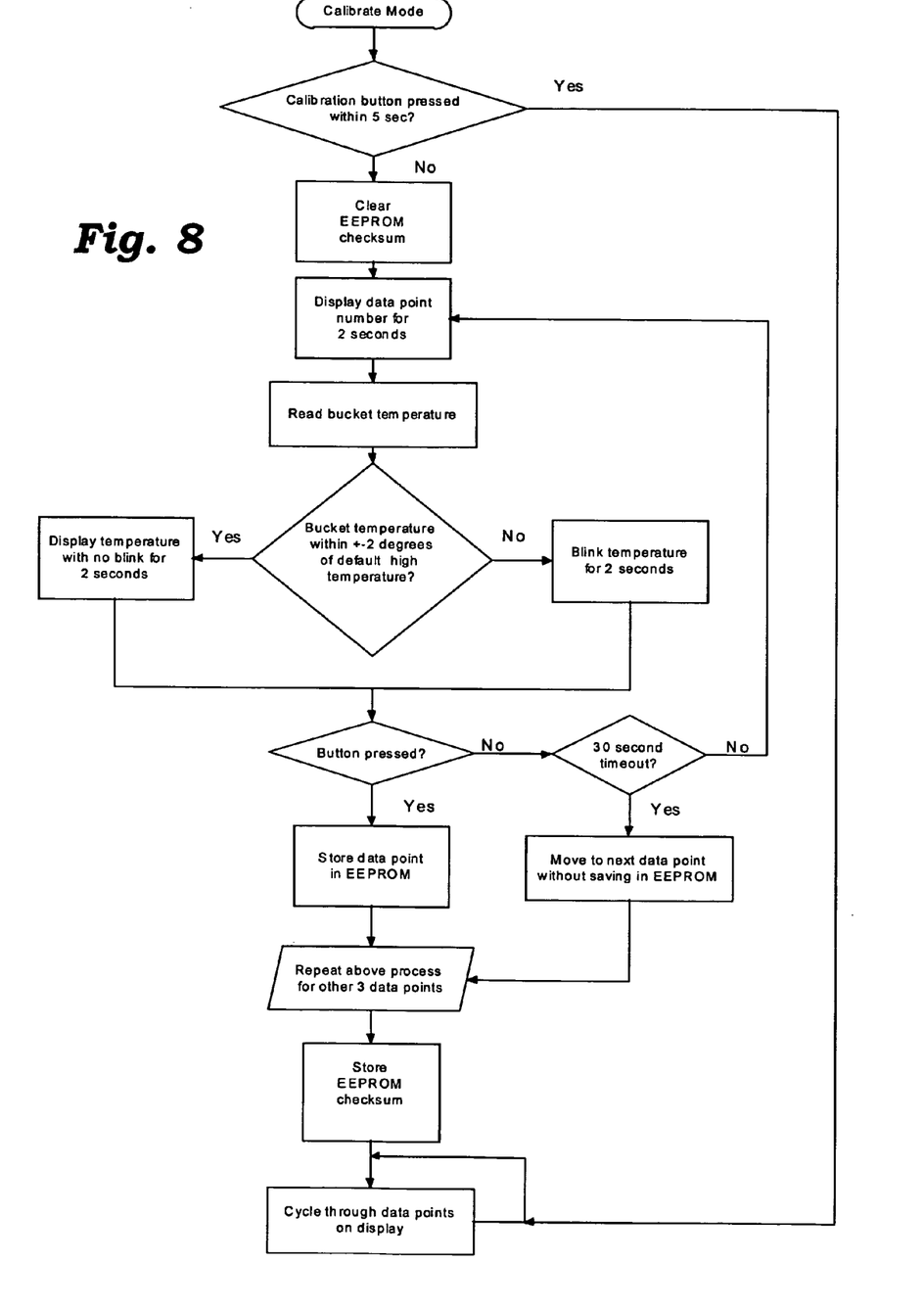
Figure 9:
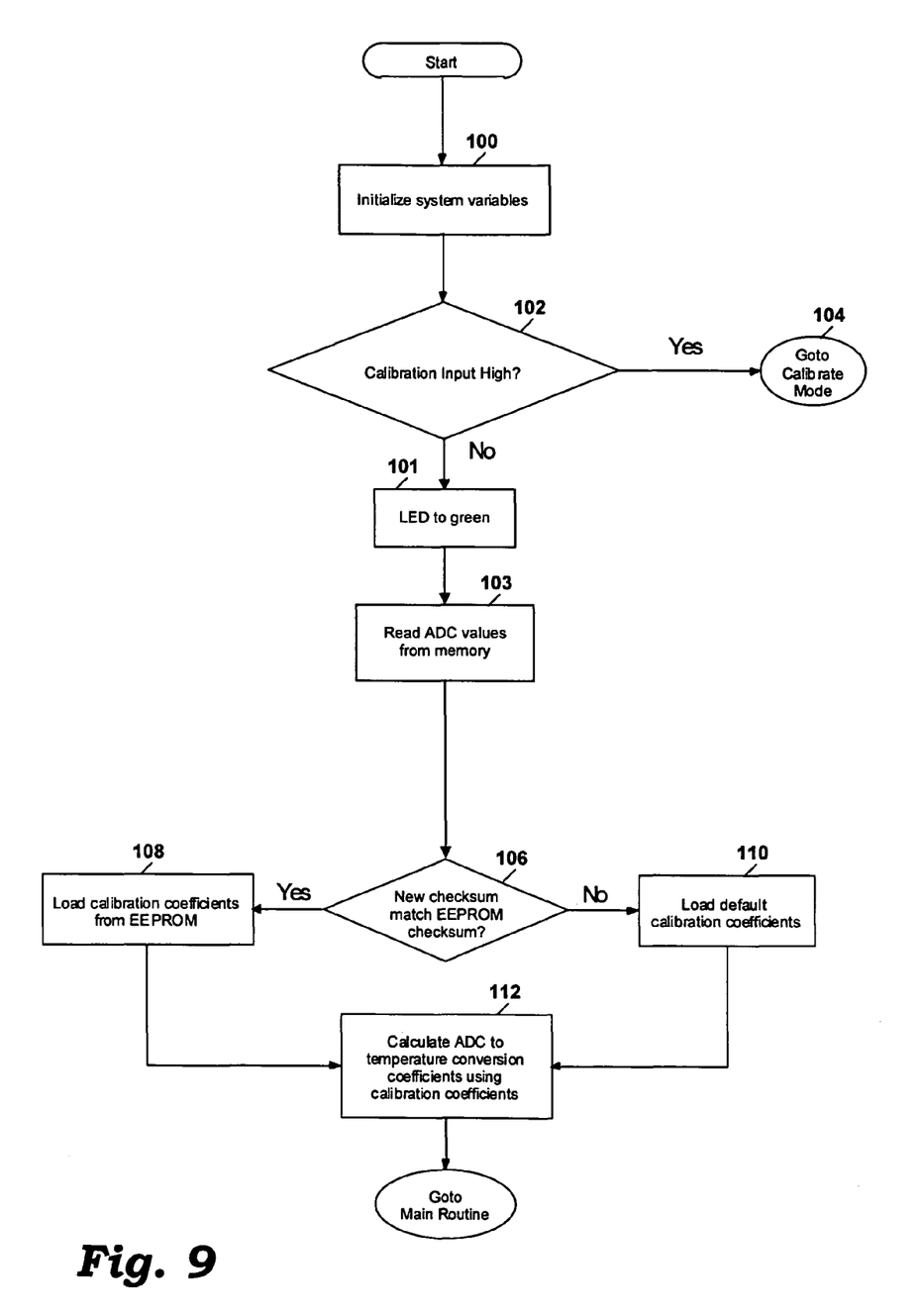

With reference to the flow diagrams of FIGS. 4-9, a preferred method of operating the device 10 is now described. For purposes of this description, it is understood that the fluid reservoir 12 has been properly filled with fluid, such as ice water or hot water. When power is initially applied to the system, an initialization routine as shown in FIG. 9 is preferably performed. According to this initialization routine, system variables are initialized (step 100), and the microcontroller 16 checks whether a calibration input value is high (+5V) (step 102). If so, calibration is needed and the system goes into a calibration mode (step 104) which is depicted in FIG. 8.

If the calibration input value is low (step 102), the system continues with normal operation and sets the LED 32 to green. The controller 16 then reads the ADC calibration values from the memory 34. For example, the calibration data points may be:

Data point 1=reservoir ADC value at 120° F.,

Data point 2=blanket ADC value at 120° F.,

Data point 3=reservoir ADC value at 38° F., and

Data point 4=blanket ADC value at 38° F.

The checksum of these data points is then compared to the checksum stored in the memory 34. If the two checksums match (step 106), the ADC calibration values in the memory 34 are loaded (step 108) and used to determine the coefficients in Equation (1). If the checksums do not match, then a default set of ADC calibration values are used (step 110).

The chosen set of ADC calibration values are used to calculate the rise, run, and Z-intercept of Equation (1) (step 112). For example:

Run=Maximum temperature−Minimum temperature=120−38=82

Rise=ADC value at 120° F.−ADC value at 38° F.=885−633=252

$Z_{intercept}$=(ADC value at 120° F.)−120×(Rise/Run)=885−120×(252/82)=516.2

In the preferred embodiment, two sets of rise, run and $Z_{intercept}$ coefficients are calculated at step 112—one set for the fluid reservoir temperature equation and one set for the blanket temperature equation.

Figure 4:
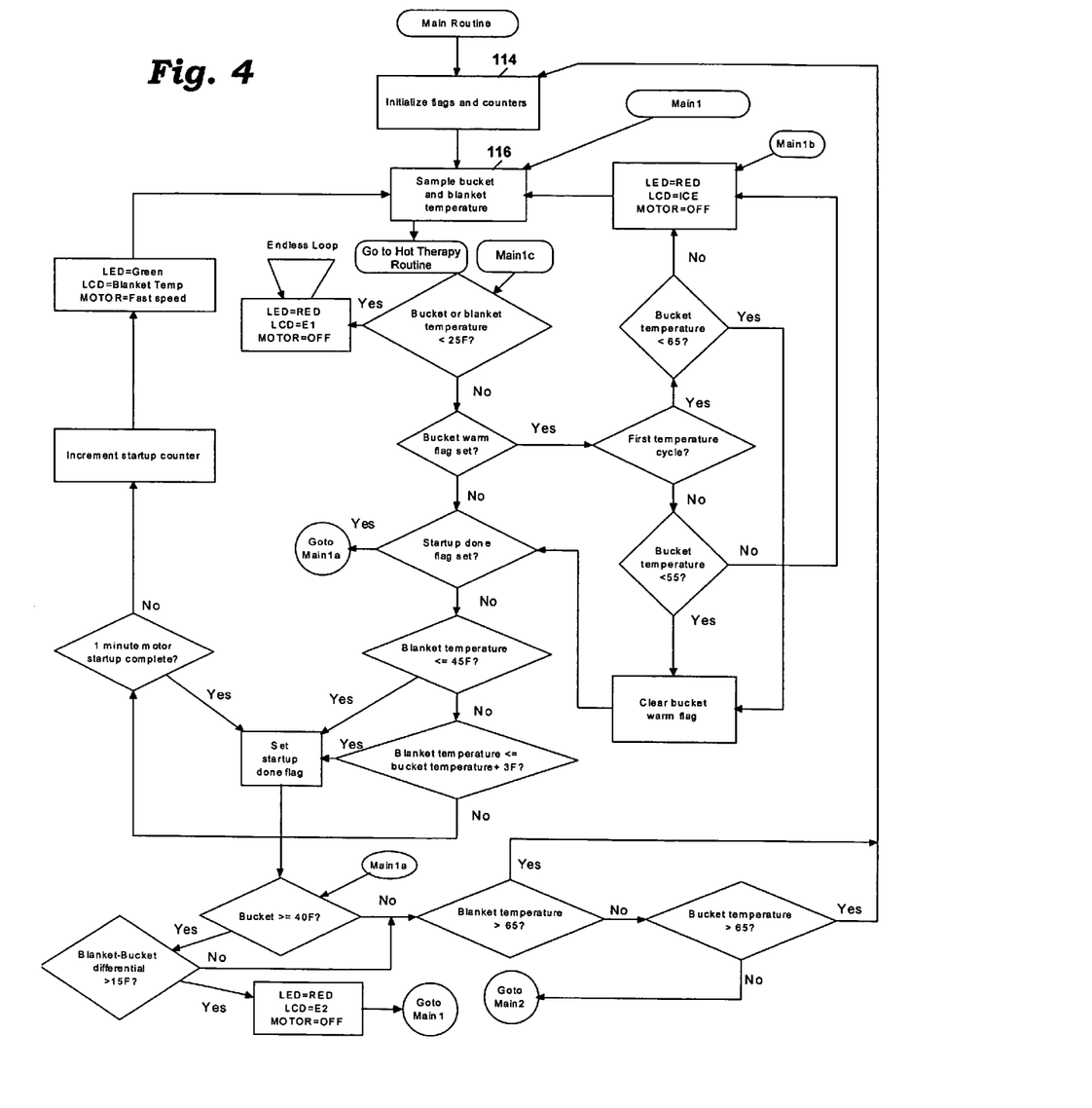
FIGS. 4-9 are flow diagrams of processes for controlling a fluid therapy apparatus according to preferred embodiments of the invention.

After these coefficients are computed, the process proceeds to what is referred to herein as the main routine, a preferred embodiment of which is depicted beginning in FIG. 4. The main routine directs operation of the microcontroller 16 to control the sampling of the blanket and reservoir temperatures, and then determine the appropriate course of action based on those temperatures. The main routine also updates the LCD display 30, the LED indicator 32, and the speed of the pump motor 19.

As shown in FIG. 4, the main routine begins by setting counters to zero and initializing flags (step 114). The flags and their functions are listed in Table III. The counters are listed in Table IV.

TABLE III

| Flag | Default | Function(s) |
|---|---|---|
| BUCKET_WARM | set | when set indicates reservoir is above warm threshold for cold therapy (≧65° F. for first cycle, ≧55° F. for all subsequent cycles)<br>cleared when reservoir temperature goes below warm threshold<br>set when unit goes into "ICE" mode |
| STARTUP_DONE | cleared | when set indicates startup period has ended<br>cleared when unit goes into "ICE" mode |
| SYS_ERROR | cleared | when set indicates a system error has occurred<br>cleared after system error condition is removed |

TABLE IV

| Counter | Function |
|---|---|
| STARTUP_COUNTER | counts startup period in one second increments after reservoir temperature goes below "ICE" threshold |
| EE_COUNT | counts a 3-minute error period in one second increments after blanket temperature goes more than 5° higher than the reservoir temperature (assuming the blanket temperature is not within its regulated temperature range) |

After the flags and counters are initialized, the main loop of the routine begins by sampling the reservoir temperature and blanket temperature based on the output signals from the sensors 24 and 26 sampled by the microcontroller 16 (step 116). In the preferred embodiment, the ADC takes 2970 samples of each temperature signal over a period of 990 milliseconds (5940 samples total). Preferably, the microcontroller 16 then computes the straight average of the 2970 ADC samples during the next 10 millisecond period. (Total cycle time=990+10 milliseconds=1 second). The average ADC value for the reservoir sensor signal and for the blanket sensor signal are then converted into corresponding temperature values based on Equation (1). Preferably, this ADC sample routine occurs once every second, and the resulting temperature values are used in the computations described hereinafter. The blanket temperature value is preferably updated on the LCD display 30 once every second.

Hot Therapy Mode

Figure 5:
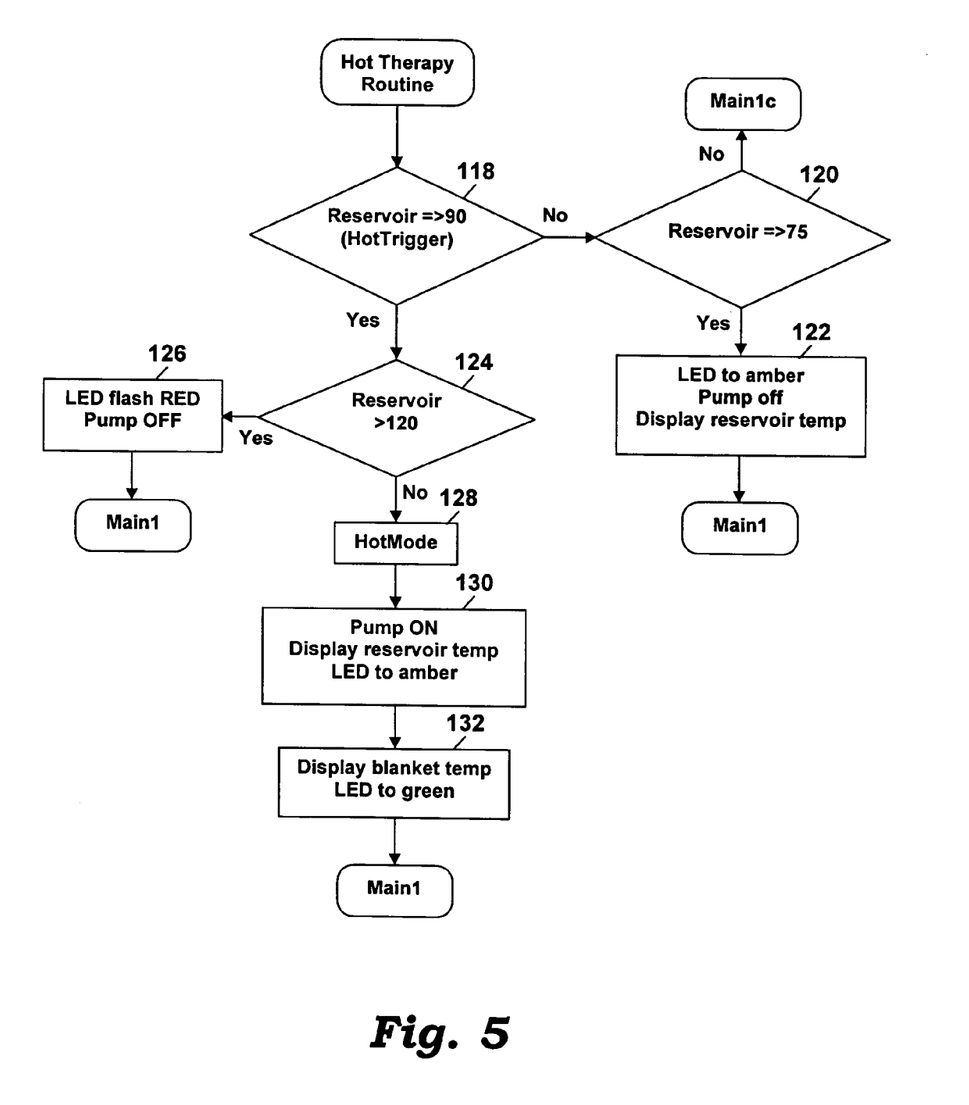
Figure 6:
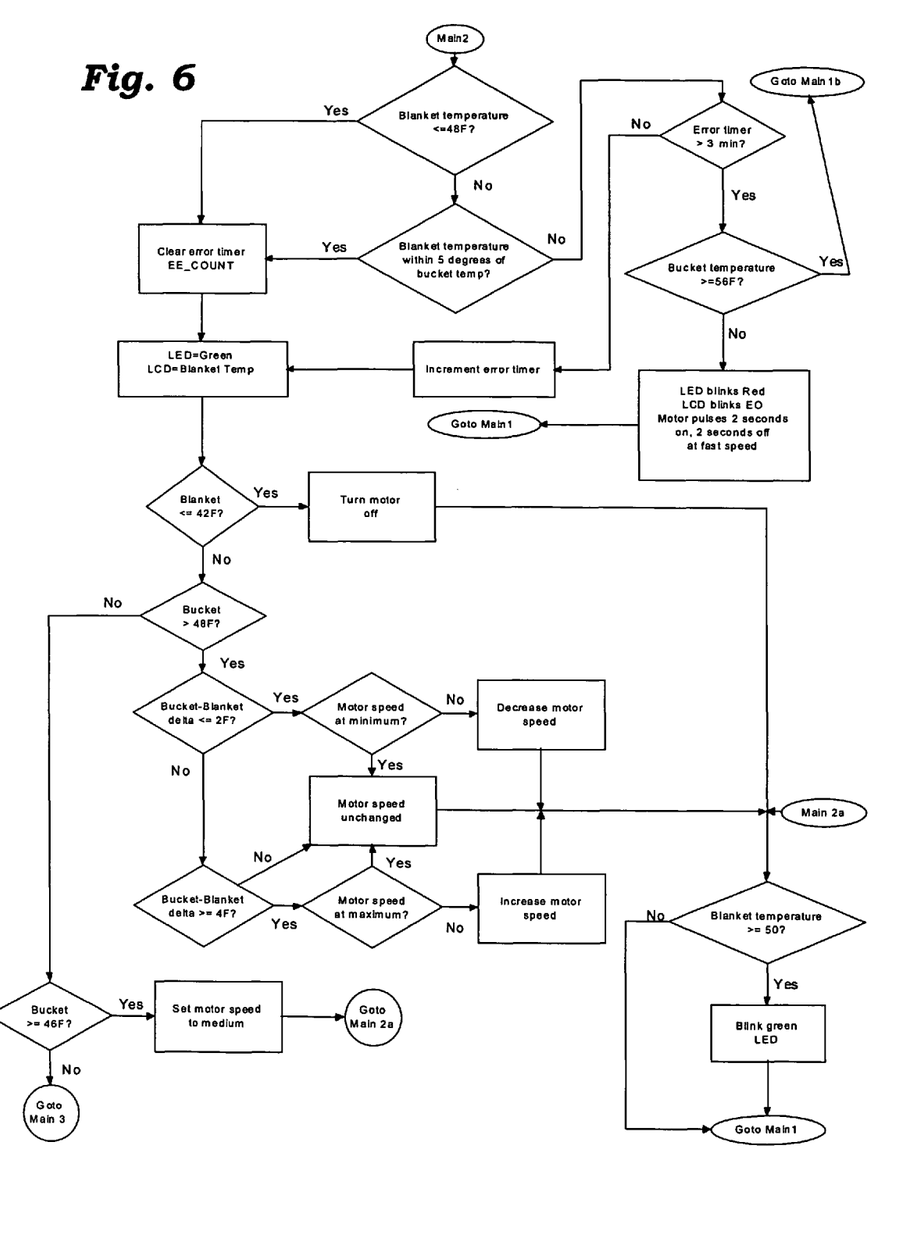
Figure 7:
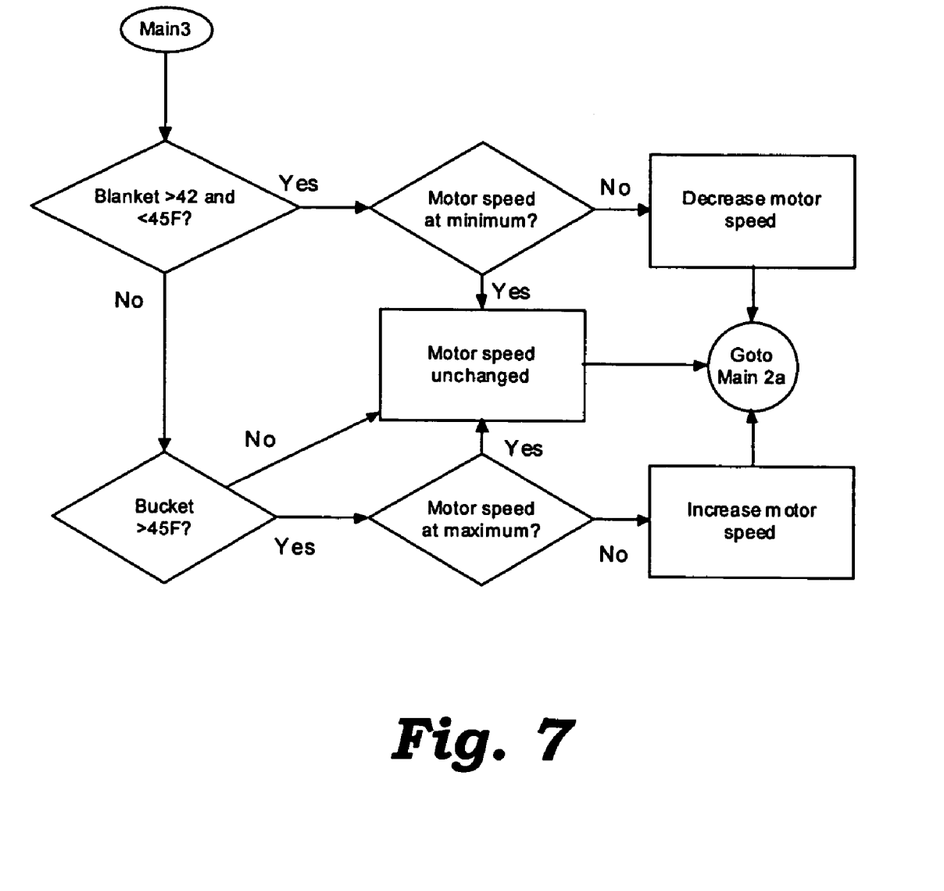

In a preferred embodiment, the process next proceeds to the hot therapy routine depicted in FIG. 5. This routine first determines, based on the temperature of the fluid in the reservoir 12, whether the device 10 has been set up to operate in the hot therapy mode, and if so, to maintain the temperature in the blanket 22 accordingly. After the reservoir temperature has been sampled (step 116 in FIG. 4), the microcontroller 16 determines whether the reservoir temperature is at least 90° F. (step 118). If not, the temperature of the fluid in the reservoir is not sufficiently hot to provide adequate heat therapy for the user of the device 10. In this situation, the microcontroller 16 next determines whether the reservoir temperature is at least 75° F. (step 120). If not, this could mean that the device is set up for cold therapy, and the process control proceeds back to the main routine at step 116 (FIG. 4). If the reservoir temperature is found to be 75° F. or more at step 120, the temperature in the reservoir is not cold enough for cold therapy and not hot enough for hot therapy. In this situation, the LED indicator 32 is set to amber, the pump motor 19 is turned off, and the reservoir temperature is displayed on the LCD display 30 (step 122). The process then preferably returns to the main routine at step 116 (FIG. 4) to sample the temperatures again. This loop continues until the power is cycled or until the fluid in the reservoir 12 is made either cold enough or hot enough for the desired therapy.

If the microcontroller 16 determines at step 118 that the reservoir temperature is at least 90° F., the microcontroller 16 then determines whether the reservoir temperature is greater than 120° F. (step 124), which would indicate that the fluid is too hot for safe use in hot therapy applications. In this case, the LED indicator is set to flash red, the pump motor 19 is turned off (step 126) and process control returns to step 116 in the main routine (FIG. 4). This loop continues until the power is cycled or until the temperature of the fluid in the reservoir 12 is reduced to less than 120° F., which is generally considered safe for use in hot therapy applications.

If the microcontroller 16 determines at step 124 that the reservoir temperature is less than 120° F., then the fluid in the reservoir 12 is within an acceptable range for use in hot therapy and the device 10 is set up to operate in hot therapy mode (step 128). In this mode, the microcontroller 16 activates the pump motor 19 to run continuously at its maximum specified speed, displays the reservoir temperature on the display device 30 and sets the LED 32 to amber (step 130) for one second. The microcontroller 16 then displays the blanket temperature on the display device 30 and sets the LED 32 to green (step 132) during the next second. At this point, the process returns to the main routine at step 116 to sample temperatures again. This loop continues as long as the temperature of the fluid in the reservoir 12 is at least 90° F. but no greater than 120° F., or until the power is cycled.

Cold Therapy Mode

When operating in the cold therapy mode, the preferred embodiment of the system 10 is generally in one of three operational modes, referred to herein as the warm mode, the startup mode and the primary operating mode.

The system is in the warm mode if the temperature of the reservoir 12 is 65° F. or greater. In this mode, the pump motor 19 is not running and the indicator "ICE" is displayed on the display device 30. This indicates to the user that ice should be added to the reservoir if it is desired to operate the system in the cold therapy mode.

Once ice is added to the reservoir and the reservoir temperature drops to less than 65° F., the system operates in start up mode. In this mode, the pump motor 19 runs at maximum power until any one of the following conditions is met: (1) the temperature of the blanket 22 reaches 45° F., (2) 3 minutes pass, or (3) the difference between the reservoir temperature and the blanket temperature is 3° F. or less. When any one of these three conditions is met, the system transitions from the start up mode to the primary operating mode.

When in the primary operating mode, the preferred embodiment of the invention operates as set forth in Table V.

TABLE V

| Reservoir Temperature | Blanket Temperature | Pump Condition |
| --- | --- | --- |
| <46° F. | ≦42° F. | off |
| | >42° F. and <45° F. | speed decrements to prevent blanket temperature from dropping further (can go down to minimum speed of 44% of maximum) |
| | =45° F. | speed remains unchanged |
| | >45° F. | speed increments to bring blanket temperature back to 45° F (can go up to maximum speed) |
| ≧46° F. and ≦48° F. | within 5° F. of reservoir temperature | runs at medium speed |
| ≧49° F. | 2° F. or more below reservoir temperature | speed decrements down to lowest speed |
| | more than 2° F. and less than 4° F. above reservoir temperature | speed remains unchanged |
| | 4° F. or more above reservoir temperature | speed increments to bring blanket temperature to within 5° F. of reservoir temperature (can go up to maximum speed) |

If the reservoir temperature or the blanket temperature goes above 65° F. while operating in the primary mode, the system will return to the warm mode and "ICE" is displayed on the display device 30. Once ice is added to the reservoir (without turning off power), the system will return to the primary operating mode after the reservoir temperature goes below 55° F. In a preferred embodiment of the invention, cycling power to the system in this situation resets the threshold to trigger warm mode operation back to 65° F.

An example of a preferred process for operating the system 10 in the cold therapy mode is set forth in the flowcharts of FIGS. 4-7. As discussed above, these flowcharts merely provide an example of a preferred method of operating the system, and the invention is not limited to the method depicted in these flowcharts.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as is suited to the particular use contemplated. All such modifications and variations are within the scope of the invention as determined by the appended claims when interpreted in accordance with the breadth to which they are fairly, legally, and equitably entitled.

What is claimed is:

1. A temperature controlled fluid therapy system comprising:
   a reservoir for containing fluid at a first temperature;
   a pump disposed within the reservoir and having an intake port and an output port, the pump for pulling the fluid from the reservoir into the intake port and forcing the fluid through the output port, the pump having a motor for driving the pump;
   a watertight blanket having an internal space through which the fluid at a second temperature may be circulated at a fluid flow rate, and having an outflow port and an inflow port that are in fluid communication with the internal space;
   an output conduit having a first end in fluid communication with the output port of the pump and a second end in fluid communication with the inflow port of the blanket;
   an intake conduit having a first end in fluid communication with the reservoir and a second end in fluid communication with the outflow port of the blanket;
   a first temperature sensor disposed within the reservoir for generating a first temperature signal related to the first temperature;
   a second temperature sensor disposed adjacent the blanket for generating a second temperature signal related to the second temperature;
   one or more analog-to-digital converters for converting the first and second temperature signals into digital signals;
   a power supply for providing power at least to the motor of the pump; and
   a microprocessor controller for receiving the digital signals corresponding to the first and second temperature signals, for determining based on the first temperature signal whether the system is to operate in a hot therapy mode or a cold therapy mode, for executing a first set of instructions if the system is to operate in the hot therapy mode and for executing a second set of instructions if the system is to operate in the cold therapy mode, and for controlling the speed of the motor based on the first or second set of instructions and on the first and second temperature signals, thereby controlling the fluid flow rate through the blanket and the temperature of the fluid in the blanket.

2. The temperature controlled therapy system of claim 1 further comprising the microprocessor controller for controlling the speed of the motor to maintain the second temperature within a hot temperature range when the first temperature is within the hot temperature range, and to maintain the second temperature within a cold temperature range when the first temperature is within the cold temperature range.

3. The temperature controlled therapy system of claim 2 wherein the hot temperature range is about 90° F. to 120° F.

4. The temperature controlled therapy system of claim 2 wherein the cold temperature range is about 45° F. to 65° F.

5. The temperature controlled therapy system of claim 2 further comprising the microprocessor controller for controlling the speed of the motor to cause the motor to stop when the first temperature signal indicates that the first temperature is below the cold temperature range by a predetermined amount.

6. The temperature controlled therapy system of claim 2 further comprising the microprocessor controller for controlling the speed of the motor to cause the motor to stop when the first temperature signal indicates that the first temperature is above the hot temperature range by a predetermined amount.

7. The temperature controlled therapy system of claim 2 further comprising the microprocessor controller for controlling the speed of the motor to cause the motor to stop when the first temperature signal indicates that the first temperature is below the hot temperature range by a predetermined amount.

8. The temperature controlled therapy system of claim 7 further comprising:
   a display device electrically connected to the microprocessor controller for displaying textual messages to a user of the therapy system; and
   the microprocessor controller for causing the display device to display a textual message indicating that hot fluid should be added to the reservoir when the first temperature signal indicates that the first temperature is below the hot temperature range by the predetermined amount.

9. The temperature controlled therapy system of claim 2 further comprising the microprocessor controller for controlling the speed of the motor to cause the motor to stop when the first temperature signal indicates that the first temperature is above the cold temperature range by a predetermined amount.

10. The temperature controlled therapy system of claim 8 further comprising:
    a display device electrically connected to the microprocessor controller for displaying textual messages to a user of the therapy system; and
    the microprocessor controller for causing the display device to display a textual message indicating that ice should be added to the reservoir when the first temperature signal indicates that the first temperature is above the cold temperature range by the predetermined amount.

11. The temperature controlled therapy system of claim 1 wherein the reservoir further comprises an interior liner and an outer jacket with a cavity between the interior liner and outer jacket.

12. The temperature controlled therapy system of claim 11 further comprising:
    the interior liner having an upper surface with an aperture therein;
    a removable insert member disposed within the aperture in the upper surface of the interior liner, the insert member including an entry port and an exit port;
    the first end of the output conduit coupled to the exit port of the insert member;
    the first end of the intake conduit coupled to the entry port of the insert member;
    the exit port of the insert member in fluid communication with the output port of the pump; and
    the entry port of the insert member in fluid communication with the reservoir.

13. The temperature controlled therapy system of claim 12 wherein the pump is suspended from the insert member by way of the output conduit.

14. The temperature controlled therapy system of claim 13 wherein the first temperature sensor is attached to the output conduit.

15. The temperature controlled therapy system of claim 1 wherein the second temperature sensor is disposed within the intake conduit adjacent the second end thereof, whereby the second temperature sensor is exposed to fluid flow within the intake conduit.

16. The temperature controlled therapy system of claim 12 further comprising:
   a printed circuit board attached to the insert member; and
   the controller disposed on the printed circuit board.

17. The temperature controlled therapy system of claim 1 further including a fluid conduit assembly comprising:
   the intake conduit;
   the output conduit; and
   an insulating jacket enclosing the intake and output conduits.

* * * * *